United States Patent [19]

Jordan

[11] 4,157,336

[45] Jun. 5, 1979

[54] CARBOXYLATE TRANSMETALLATION-ESTERIFICATION PROCESS

[76] Inventor: Robert K. Jordan, Carlton House, Suite 1431, 550 Grant St., Pittsburgh, Pa. 15219

[21] Appl. No.: 758,082

[22] Filed: Jan. 10, 1977

[51] Int. Cl.$^2$ .......................... C07F 1/08; C07F 3/08; C07F 11/00; C07F 15/02

[52] U.S. Cl. .................... 260/429 R; 260/429.9; 260/438.1; 260/438.5 R; 260/439 R

[58] Field of Search .................. 260/491, 482 C, 542, 260/438.1, 439 R, 438.5 R, 429 R, 429.9

[56] References Cited

U.S. PATENT DOCUMENTS

| | | | |
|---|---|---|---|
| 2,156,598 | 5/1939 | Miescher et al. | 260/431 |
| 2,373,583 | 4/1945 | Loder | 260/542 |
| 2,472,434 | 6/1949 | Pechukas | 260/491 |
| 2,659,745 | 11/1953 | Vaughan | 260/440 |
| 2,699,427 | 1/1955 | Smith et al. | 252/33.6 |
| 2,822,348 | 2/1958 | Haslam | 260/491 X |
| 2,885,433 | 5/1959 | Hagemann et al. | 260/482 |
| 2,886,591 | 5/1959 | Lautenschlager et al. | 260/486 |
| 2,931,819 | 4/1960 | Mayne et al. | 260/491 X |
| 3,296,130 | 1/1967 | Gee et al. | 252/33.6 |
| 3,328,439 | 6/1967 | Hamilton | 260/491 X |
| 3,480,656 | 11/1969 | Heiss | 260/429.7 |
| 3,493,610 | 2/1970 | Coffield | 260/542 |
| 3,699,155 | 10/1972 | Brady | 260/491 |
| 3,784,578 | 1/1974 | Swodenk et al. | 260/491 X |

Primary Examiner—Helen M. S. Sneed

[57] ABSTRACT

A process in which a metal carbamate, especially an N-mono- or N-di-hydrocarbaryl carbamic acid metal salt, is combined with an ester or amide of a carboxylic acid to produce a metal carboxylate and a urea or an ester of a carbamic acid. The carbamate esters of acidic hydroxyl compounds, usually phenolics, can further decompose to the corresponding phenol and isocyanate, or, the carbamate ester may be combined with ammonia, a primary amine or secondary amine to produce the corresponding hydroxylated hydrocarbaryl and urea. A variation includes transesterification-metallation between carboxylate esters and metal salts of carboxylic acids.

12 Claims, No Drawings

CARBOXYLATE TRANSMETALLATION-ESTERIFICATION PROCESS

This invention relates to a process for coverting metal carbamates or carboxylates with esters or amides of carboxylic acids to ureas, carboxylate esters or carbamate esters, and decomposition products thereof, and coproduct metal carboxylates, and decomposition products thereof.

Carbamate esters are of growing interest and have established markets as pesticides, for example the alpha-naphthyl ester of N-methyl carbamate enjoys a market of a hundred million pounds annually. But by conventional processes these are expensive to make, involving the expensive and hazardous phosgenation of amines. Similarly, isocyanates such as toluene diisocyanates and polymethylenepolyphenylene polyisocyanates, used respectively in flexible and rigid polyurethane foams, are also made by the same process of amine phosgenation.

Urea is well known as a fertilizer and N-substituted, including mono-di-, tri and tetra hydrocarbaryl substituted ureas have been used as stabilizers in elastoners and plastics, and in themselves can be reacted further to other products. For example, N,N'-diphenyl urea reacts with phosgene to provide phenyl isocyanate, used mainly as an intermediate in pharmaceuticals, but which if cheap could enjoy a vast market in copolymers.

Carboxylic acid esters have a wide range of uses. The lower esters such as methyl acetate, are widely used solvents and methyl formate is often further reacted with ammonia to produce formamide, useful as a solvent and also potentially a valuable intermediate to cheap and less energy intensive hydrogen cyanide. Esters of aromatic acids such as butyl phthalate, are often used as plasticizers for plastics and explosives. But some esters are more easily and cheaply made than others.

Ketones, especially acetone and methyl ethyl ketone, are also widely used as solvents, for example for printing inks. Metal carboxylates are also often used as stabilizing additives or lubricants for plastics.

Therefore, it is an object of my invention to provide a new and improved process for the production of esters of carbamic acids.

It is another object to provide a new and improved process for the production of metal carboxylates.

It is yet another object to provide a new and improved process for the production of isocyanates.

My invention is a process for the coproduction of metal carboxylates and esters of carbamic acids, and decomposition products thereof, comprising combining an ester of a carboxylic acid and a a metal salt of a carbamic acid.

I have discovered unexpectedly that when the sodium salt of N-methyl carbamate is mixed with the methyl ester of trifluoroacetic acid, practically independent of the ratio, although a 1:1 mole ratio is ideal, an interchange takes place even at the low refluxing temperature of methyl trifluoroacetate, resulting in methyl N-methyl carbamate and sodium trifluoroacetate, which are easily separated by distillation or precipitation. This is rather clear since methyl trifluoroacetate distills at about room temperature compared to about 155° C. for methyl N-methyl carbamate and of course the salts of either acid are relatively insoluble in either ester. The interchange is accelerated by increasing temperature, although this necessitates operation under pressure to prevent loss of methyl trifluoroacetate before it has a chance to react. At very high temperatures the process is quite rapid, although again this necessitates operating at up to 50 atm. Nonaqueous solvents may be utilized, especially polar solvents like dimethylsulfoxide, acetonitrile, ethyl ether, dioxane, alcohols, ketones, etc. often significantly accelerate the process. Catalysts which are known as transesterification catalysts also assist the interchange, for example titanium esters. This is especially surprising in that these would be expected to participate in the process, and in fact to a limited extent do.

In Ser. No. 433,296, I have disclosed an economic new process for producing metal salts of N-substituted carbamic acids from the amine, cheap salt and carbon dioxide. N-mono- and N-disubstituted carbamic acid metal salts including alkyl, aryl, heterocyclic, mixed and also further substituted such as hydrocarbaryl and halogenated, may be used in this novel process. Since esters of carboxylic acids are very easily and inexpensively made, the instant invention is a cheap route to carbamate esters, e.g., naphthyl methylcarbamate insecticide. Such carbamate esters are made conventionally by a very expensive and hazardous process entailing phosgenation (with phosgene, $COCl_2$) of the amine to either the carbamoyl chloride or its decomposition product, the corresponding isocyanate, followed by reaction or addition of the alcohol, or phenol or naphthol;

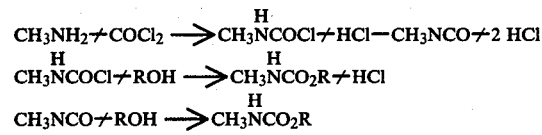

Moreover there is another extrordinary advantage. Carbon monoxide is easily added to methanol (and other alcohols and phenols and naphthols) to provide the formate ester. Thus by the instant process methyl formate and sodium N-methyl carbamate interact to yield the methyl ester of N-methyl carbamic acid and sodium formate. As explained in my copending application Ser. No. 433,296 filed Jan. 14, 1974, anhydrous sodium formate is a valuable intermediate to caustic soda, soda ash, oxamide and other chemicals because it fuses at about 400° C. to sodium oxalate and hydrogen.

A great variety of esters of carboxylic acids have been tried with a fair range of metal carbamates and some exchange is always observed. Nor is it all a matter of using an ester of a strong acid such as trifluoroacetic acid or oxalic acid because practically all carboxylic acids are stronger than the carbamic acids, which is of course evidenced by the fact that the free carbamic acids aren't normally observed. Rather important to a full understanding of the process is the fact that even among carboxylic esters and salts the analogous interchange is observed, and among weak acids, for example methyl benzoate and sodium acetate very clearly yields methyl acetate and sodium benzoate. Most simply the methyl acetate is only flashed off the mixture. The rate again is temperature dependent. And while it is possible to utilize very high temperatures, say 500° C., for short residence times, in this instance it is desirable to operate at about the boiling temperature of methyl benzoate, 195.5° C. With the formation of carbamate esters the selection of an operating temperature is more complex, even the methyl ester of carbamic acid boils at 177° C. which compares to the 31.5° C. boiling temperature of methyl formate.

Fortunately the exchange between carboxylic esters and metal salts of carbamic acids takes place in the liquid phase over a wide range of temperatures, possibly as low as −30° C., albeit slowly, and there are few problems encountered if high temperature operation is utilized, since the pressures required even in using methyl formate at high temperature would not normally expected to exceed a few hundred atmospheres. A further advantage lies in the selection of the metal salt of the carboxylic or carbamic acid. The alkaline earth salts of carbamic acids work very well with oxalate esters and phthalic esters, especially the calcium salt. The usual transition metal salts, particularly trivalent metal carbamates may tend to react rapidly because of steric considerations. Iron, manganese and cadmium salts were among those utilized, to include both bi- and tri-valent metals.

There is a special advantage to conducting the process with arylesters of carboxylic acids and metal salts of either N-alkyl or N-aryl carbamic acids. This arises from the fact that at high temperatures the aryl esters of any of the carbamates having a hydrogen on the nitrogen atom because in essence these are "blocked" isocyanates that tend to decompose on heating,

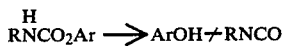

to the corresponding phenolic or naphthoic and isocyanate. And separation can be easy, for example methyl isocyanate boils about 60° C. and phenol at about 182° C. Moreover, since aryl esters based on naphthols and phenols have relatively high boiling temperatures, extrordinarily high pressures are not required. However, aryl esters are slower in the process than simple lower alkyl esters. But on the other hand there is a temperature range at which the blocked isocyanates begin to decompose into the isocyanate and hydroxy compound, much depending on the acidity of the phenolic or naphthoic compound, but possibly as low as about 100° C. for the more volatile isocyanates such as isocyanic acid or methyl isocyanate.

Another force to be reckoned with is the tendency of the metal ions to catalyze isocyanate reactions, for example trimerization to very stable isocyanurates, especially catalyzed by potassium and zinc cations to mention a few. Further, isocyanates are stabilized by acids, especially acid halides, but in the systems of this invention such acids interefere.

Polycarbamic acid salts may be utilized in the process, anything from two, as in hexamethylene dicarbamic acid salts, to polymers containing as many as hundreds of carbamate groups. Some of the amines forming the basis of polycarbamates includes hexamethylene diamine, 2,4- and 2,6-toluenediamines, m-xylyldiamine (alpha,alpha'-m-xylenediamine), methylene bis-(aniline) and other amines from the condensation of aniline with formaldehyde, all of which form metal salts and exchange to produce esters which have a free hydrogen on the carbamate nitrogen, and which can, if the corresponding hydroxyl compound is sufficiently acidic, decompose to isocyanates.

Lactones, polyesters of polyols, gylcolic acid polymers; of ethylene glycol, bisphenol-A and resorcinol to polymers containing hundreds of carboxyl groups may be used with mono- and poly-carboxylic acids, for examples such dicarboxylic acids as oxalic acid, isophthalic acid and methylene bis-(benzoic acid) to polyacids such as acrylic acid polymers and copolymers.

The process may be conducted using one of the esters as the liquid media, or a great variety of solvents may be utilized. As noted, some have accelerating effects on the interchange, especially highly polar inert solvents, while others have a retarding effect, for example parafinic oils. But while the polar solvents are called inert because they do not in fact react with the intermediates of the process, nonetheless may act as catalysts. Thus dimethyl sulfoxide, crown ethers, linear poly(alkylene oxide) compounds such as heptaethylene glycol dimethyl ether or even ester terminated products (which to a minor extent react), alcohols including the poly(alkylene oxide) glycols, ketones, less active esters than those employed for the interaction, dioxane, alkyl ethers, aryl ethers are some of those containing oxygen which act to a minor or considerable degree in promoting the kinetics of the process. The use of some of the more active compounds should rightly be termed catalysts rather than solvents, especially the crown ethers, linear poly(alkylene oxide) compounds, dimethyl sulfoxide, dioxane, others in that they enable the use of what normally would be considered inhibiting solvents with little or no loss in activity. For example in the alkali metal carbamate salts of sodium or potassium, 18-crown-6 is highly effective as a solvent-catalyst, but additionally a hydrocarbon such as toluene or mixture such as kerosine may be added. Alone such solvents would act to retard the process.

A variety of nitrogen containing solvents may be employed in the process and some have accelerating effects, especially the so-called "cage" compounds which are modified crown ethers. Others include acetonitrile, acetamide, pyridine, dimethylformamide, triethyl amine and nitrobenzene. Halogenated solvents and especially some of the chlorofluorocarbons and ethylene dichloride to the extent that conditions are utilized that avoid cation interaction to any significance. However, there can be no question but what a surprising number of solvents under extreme conditions can interfere. In fact, they often point out other heretofore unknown or unappreciated processes. Particularly akin are amides.

Acetamide and sodium N-methyl carbamate in 15-crown-5 interact to decisively form methyl urea and sodium acetate. Even dimethyl formamide and carbazole work, but clearly the most important of these from a commercial point of view is the interaction of formamide and a metal carbamate to produce urea and sodium formate. And while no catalyst is necessary for any of the reactions, most are greatly improved by them. Since urea does not distill without decomposition, and even formamide tends to decompose at higher temperatures to hydrogen cyanide, it is preferable to utilize an oxygenated organic solvent in which urea is relatively insoluble. But the process can be conducted using formamide and an alkali, alkaline earth or other bivalent or trivalent metal salt of carbamic acid with or without a solvent and the products separated after the process is essentialy completed. For example by selective extraction of the urea with methanol or ethanol in which solvents sodium formate, and practically all other metal formates, is poorly soluble, potassium formate being a notable exception. But liquid ammonia could be the extractant for urea and even potassium formate is insoluble in that solvent.

The use of carboxylic esters with carboxylic acid metal salts was noted earlier, the example being methyl benzoate with sodium acetate which is an excellent one in that the course of the process can be followed easily using a gas chromatograph to measure the methyl acetate driven off. As expected, increasing temperatures result in increasing process rates. Using higher esters, for example dimethyl terephthalate with metal salts of lower aliphatic carboxylic acids, again including the mono, bi- and tri-valent metal salts, the process can be easily studied at somewhat higher temperatures under a vacuum. And there is an accelerating effect, probably a reflection of withdrawing one of the products from the system such as is found in using the other systems with metal carbamates where one of the products is precipitated, decomposed or otherwise removed.

The nature of the hydroxyl compound is of the utmost importance in the production of isocyanates via the decomposition of the esters of carbamic acids as formed from esters of carboxylic acids with metal salts of carbamic acids. Since the most acidic hydroxyl compounds are phenol or substituted phenols or naphthol or substituted naphthols with relatively high boiling temperatures, and since rapid decomposition requires ideally temperatures over 200° C., halogenated and alkylated compounds of these are useful. And the esters of these made from the more volatile acids such as formic acid, trifluoroacetic acid and acetic acid are also sufficiently volatile at the high temperatures desirable for thermal dissociation of the carbamate ester as to suggest adding the carboxylic ester as a gas to molten metal carbamates, or metal carbamates suspended or dissolved in a media which is liquid under the conditions used in the process. For example 4-tolyl acetate boils at 212° C. and as a gas at about 250°–300° C. may be bubbled into the bottom of a heated tower which is supplied near the top with the sodium salt of N-methyl carbamate and equipped at the top to take off the product gas mixture. The conditions may be used to maintain the sodium acetate molten so that it can be continuously removed from near the bottom. The methyl isocyanate and phenol having greatly different boiling temperatures can easily be separated by selective condensation before significant recombination has taken place. Thus it is seen that a continuous process is had. The production of esters of carbamic acids and metal carboxylates is more simply made continuous by taking off the gaseous product, for example butyl N-butyl carbamate which distills at about 90° C. at 3 mm Hg. But when very high temperatures are utilized care must be taken to select conditions in terms of contact times or residence times. For example, while sodium formate melts at 256° C. it slowly decomposes to sodium carbonate and at 400° C. it very rapidly fuses to sodium oxalate with the evolution of hydrogen and further if the sodium oxalate is not rapidly cooled it too decomposes to sodium carbonate. But most metal carboxylates undergo the Wurtz reaction whose products would not interefere in a single step process of this invention. From calcium carbamate and ethyl acetate at 300°–500° C./1 hr-several minutes residence time would produce both ethyl carbamate and acetone in either a liquid process under pressure or a fluid bed process. A two step process may be worked out, for example to produce a carbamate ester and sodium formate in one step and then fuse the latter to sodium oxalate and hydrogen is a separate step, but this too could be done in a single step process.

Clearly the process for carbamate esters and metal carboxylates can be made continuous even without the expedient of distilling off the carbamate ester or its decomposition products. One simple method is to crystallize out the metal carboxylate. Yet another it is possible to convert the carbamate ester into yet another product, for example, methyl carbamate and ammonia would provide urea and methanol. The ammonia can be added to the metal carboxylate-carbamate ester and the metal carboxylate being of low solubility separated out, after which the methanol can be distilled away from the urea. A primary or secondary amine may be used instead of ammonia.

The ideal mode of the process in terms of simplicity is that of a liquid phase system with separation being effected on the products continuously, intermittantly or batchwise by techniques well known in the art such as distillation, crystallization, liquid extraction, liquid-liquid extraction, etc. Depending on what is desired from the process, i.e., the two basic products, or their decomposition products.

Alternatives to the purely liquid phase process include liquid-solid gas-solid, gas-liquid systems. The temperature may range from well below 0° C., say −30° C., to well over 500° C., the residence time ranging from days down to a few seconds at a pressure ranging from less than a mm of Hg to several hundred atmospheres. Clearly too the processes can be conducted mixed, i.e., carboxylate ester(s) with metal carbamate-metal carboxylate systems, amide-metal carbamate-metal carboxylate, etc.

New compositions are obtainable from the process when the carboxylate ester-metal carbamate system is employed using lactones and polyesters made from condensing glycolic acid or other hydroxycarboxylic acid. The simplest $H_2NCO_2CH_2CO_2Na$ or p-$H_2NCO_2C_6H_4CO_2K$ for an arylene compound. Clearly using diketene unsaturated compounds are obtained, for example $CH_3NHCO_2C(CH_3)=CH_2CO_2Z-nO_2CCH_2=C(CH_3)O_2CNHCH_3$, and using polymers leads to compositions of the formula,

where M is a mono-, bi-or tri-valent metal, R and R″ are hydrocarbylene radicals which may contain unsaturation, halogen atoms, nitro groups and other groups which do not significantly interfere with the process of their manufacture, R′ is hydrogen or hydrocarbyl radicals and n may range from 1 to 200. A more generalized formula,

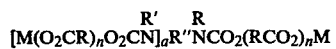

uses similar terminology, differing in that a is 0 or 1, R″ is a hydrocarbylene or hydrocarbyl radical, again containing optionally unsaturation, halogen atoms, etc, M is an equivalent of a metal selected from mono-, bi- and trivalent metals, the Rs and R′s and ns are not necessarily the same. Examples of the metal salts, which may be mixtures of metal cations, include alkali metal, alkaline earth metal, copper I and II, iron II and chromium III salts, all capable of being made in the process of this invention. These salts are useful as insecticides.

According to the provision of the patent statutes, I have explained the principle of my invention and have illustrated and described what I now consider to represent its best embodiment. However, I desire to have it understood that within the scope of the appended claims, the invention may be practiced otherwise.

I claim:

1. A process for the coproduction of metal carboxylates and esters of carbamic acids, and decomposition products thereof, comprising combining an ester of a carboxylic acid and a metal salt of a carbamic acid.

2. The process of claim 1 using a nonaqueous media.

3. A process for the coproduction of esters of carboxylic acids and metal carboxylates, and decomposition products thereof, comprising combining a metal salt of a carboxylic acid and an ester of a carboxylic acid.

4. The process of claim 3 using a nonaqueous media.

5. A process for the coproduction of ureas and metal carboxylates, and decomposition products thereof, comprising combining an amide of a carboxylic acid and a metal salt of a carbamic acid.

6. The process of claim 5 using a catalyst.

7. The process of claim 5 using a nonaqueous media.

8. A process for the coproduction of ureas and metal carboxylates comprising, a. combining an ester of a carboxylic acid and a metal salt of a carbamic acid to produce a metal carboxylate and an ester of a carbamic acid and b. adding ammonia or a primary or secondary amine to said ester of a carbamic acid to produce a urea.

9. A compound having the formula

where R and R'' may be hydrocarbylene R' and R'' may be hydrocarbyl, R' may also be be hydrogen, M is an equivalent of mono-, bi- and trivalent metals, n is from 1 to 200 and a is 0 or 1.

10. A process for the exchange of carboxylic acid metal salts and esters comprising combining an ester of one carboxylic acid and the metal salt of at least a second carboxylic acid in the presence of an essentially inert polar compound, said exchange being conducted in a liquid media.

11. The process of claim 10 wherein the polar compound is selected from those tending to form complexes with the metal cation of the metal salt.

12. A process for the exchange of carboxylic acid metal salts and amides comprising combining an amide of one carboxylic acid and a metal salt of at least a second carboxylic acid, said exchange being conducted in a liquid media.